United States Patent
Lockart

(10) Patent No.: US 11,253,385 B1
(45) Date of Patent: Feb. 22, 2022

(54) BRACE WITH RESISTANCE BAND

(71) Applicant: Brice W Lockart, Tallahassee, FL (US)

(72) Inventor: Brice W Lockart, Tallahassee, FL (US)

( * ) Notice: Subject to any disclaimer, the term of this patent is extended or adjusted under 35 U.S.C. 154(b) by 221 days.

(21) Appl. No.: 16/449,323

(22) Filed: Jun. 21, 2019

(51) Int. Cl.
*A61F 5/01* (2006.01)

(52) U.S. Cl.
CPC .... *A61F 5/0123* (2013.01); *A61F 2005/0167* (2013.01); *A61F 2005/0169* (2013.01)

(58) Field of Classification Search
CPC ................ A61F 5/0123; A61F 5/0125; A61F 2005/0137; A61F 2005/0167; A61F 2005/0169; A61F 5/04; A61F 5/042; A61F 5/05; A61F 5/058; A61F 5/05825; A61F 5/05841; A61F 5/0585; A63B 21/04; A63B 21/0407; A63B 21/0414; A63B 21/055; A63B 21/0552; A63B 21/0557; A63B 23/04; A63B 23/0405; A63B 23/0494
USPC .......................................................... 602/16
See application file for complete search history.

(56) References Cited

U.S. PATENT DOCUMENTS

| | | | |
|---|---|---|---|
| 4,606,542 A * | 8/1986 | Segal .................... | A61F 5/0125 482/105 |
| 5,167,612 A | 12/1992 | Bonutti | |
| 5,203,754 A | 4/1993 | Maclean | |
| 5,213,094 A | 5/1993 | Bonutti | |
| 5,685,830 A | 11/1997 | Bonutti | |
| 5,865,714 A | 2/1999 | Marlowe | |
| 6,063,048 A | 5/2000 | Bodenschatz et al. | |
| 6,117,097 A * | 9/2000 | Ruiz ...................... | A61F 5/0109 602/20 |
| 6,537,237 B1 | 3/2003 | Hopkins et al. | |
| 7,048,704 B2 | 5/2006 | Sieller et al. | |
| 7,156,819 B2 | 1/2007 | Sieller et al. | |
| 7,608,051 B1 | 10/2009 | Nace | |
| 7,931,609 B2 * | 4/2011 | Blanchard ........... | A61F 5/05841 602/21 |
| 7,963,933 B2 | 6/2011 | Nace | |
| 8,057,414 B2 | 11/2011 | Nace | |
| 8,308,669 B2 | 11/2012 | Nace | |
| 8,376,974 B2 * | 2/2013 | Nace ..................... | A61F 5/0123 602/16 |
| 9,114,277 B2 | 8/2015 | Goeckel | |
| 9,220,623 B2 * | 12/2015 | Burns ................ | A63B 21/0552 |
| 9,452,075 B2 | 9/2016 | Berg | |
| 10,085,869 B2 | 10/2018 | Nace | |
| 2011/0105969 A1 | 5/2011 | Nace | |
| 2013/0110020 A1 | 5/2013 | Ingimundarson et al. | |
| 2013/0245524 A1 * | 9/2013 | Schofield .............. | A61F 5/0127 602/16 |

(Continued)

*Primary Examiner* — Camtu T Nguyen
(74) *Attorney, Agent, or Firm* — Peter Loffler

(57) ABSTRACT

A brace assists a user in regaining extension and hyperextension flexibility in an injured joint as well as aiding in resistance training in order to regain lost muscle mass about the joint. The system uses a pair of plates that each attach to a lateral side of one of the limb-encircling sleeves of the brace. An interchangeable resistance band is attached to each plate, either in the posterior or anterior position. The resistance band introduces static loading when the user is at rest as well as dynamic loading when the user is utilizing the joint. A pivot system can be used to offer the resistance band a medially located pivot point so that the resistance band offers variable resistance during dynamic loading.

3 Claims, 5 Drawing Sheets

(56) References Cited

U.S. PATENT DOCUMENTS

| | | | | |
|---|---|---|---|---|
| 2015/0051527 A1* | 2/2015 | Potter | ................... | A61F 5/0125 |
| | | | | 602/16 |
| 2016/0256310 A1* | 9/2016 | Blecher | ................ | A61F 5/0123 |
| 2016/0361222 A1* | 12/2016 | Publicover | ............ | A61F 5/0123 |

* cited by examiner

BRACE WITH RESISTANCE BAND

BACKGROUND OF THE INVENTION

1. Field of the Invention

The present invention relates to a brace, such as a knee brace, that has one or two laterally positioned removable resistance bands that assist a patient who has undergone a knee procedure or otherwise suffered a knee injury in regaining extension and hyperextension flexibility as well as assist the patient in regaining lost muscle mass in the leg muscles about the knee.

2. Background of the Prior Art

When a patient has a knee procedure performed, the patient is fitted with a brace immediately thereafter in order to keep the operated upon knee and/or limb from being injured. A typical knee brace comprises an upper sleeve that encircles the patient's leg above the knee and a lower sleeve that encircles the patient's leg below the knee. A hinge system comprises one or more typically hinges that each connect the upper sleeve with the lower sleeve and allow articulation between the two sleeves about the knee, the hinges placed on opposing lateral (side) portions of the knee brace. The knee brace protects the patient by limiting the joint range of motion through a locking system at variable degrees as prescribed by their physician relative to their progression in the rehabilitation process. The locking system is part of the hinge system. The current brace models provide a range of motion anywhere from about −10 degrees (hyperextension) to 120 degrees of flexion. Elbow braces are structured similarly and function in similar fashion.

While current braces, which come in a variety of architectures, tend to be very good at protecting the knee (or elbow) and the surrounding limb from injury, current braces serve primarily as safety systems while the patient's joint heals during the immediate post-operative period. The brace does not address the rehabilitative process necessary for the patient.

One of the most important prerequisites to progressing through the knee rehabilitation process in the early stages of post-operation or post-injury to the knee is regaining the same extension or hyperextension on the knee similar to the contralateral side. Every step an individual with a healthy knee takes, requires the knee to hyperextend, or "lockout." Without the ability to do this, many issues can arise in a person's gate such as causing overuse injuries through compensation of the healthy knee as well as developing a limp due to the repaired knee's inability to function in a similar manner to the function of the person's healthy knee.

There are known techniques to "stretch" the knee joint back out to a normal level of hyperextension but such techniques are considered by many to be very primitive and somewhat barbaric as they place stresses on the knee joint, with little, if any, quantifiable loading measures that can be used by medical personal to track progress and effectiveness of the rehabilitation process. In many of the known techniques, forcing the knee to hyperextend requires intense, painful, physical therapy. An example of such a technique has a therapist press down on the knee joint while the patient sits upright on a bench with the patient's leg extended. Another technique has the patient prop his or her foot up while seated and strap a belt or other tether around the knee between the seat and the object the foot is propped up on. The therapist then tightens the strap down to force the knee to straighten, or lock out, with the patient being forced to stay in that position for a specified period of time to maintain the tension being applied by the strap. Another technique has the patient laying supine on a table with his or her feet hanging off the table with the therapist hanging a weight off of the patient's foot in order to force the knee to hyperextend. The patient is forced to stay in this relatively painful other position for a specified period of time to hold the stretch being produced by the weight.

At some point during the rehabilitation process, the patient needs to engage in resistance training in order to reverse the muscle atrophy experienced by the leg muscles post-surgery. Typically, the patient engages in open-chain kinetic exercises using appropriate open-chain exercise machines. During this phase of rehab, the patient must be carefully monitored in order to avoid any sheering or other damage to the joint.

Conventional open-chain machines, such as leg curl or extension machines, do a great job of isolating the muscles around the joint, but force the upper portion of the limb above the joint to be fixated against a seat or pad. The machine then applies resistance to the most distal point of the lower limb away from the pivot point of the joint (typically around the ankle). Unfortunately, this process can cause a significant sheer effect on the knee so as to reinjure the knee with the attendant potential of having to once again repair the knee. Other muscle strengthening techniques are available but are relatively low impact and non-invasive in comparison to the machines, so that muscle mass regain takes significantly longer compared to using the open-chain machines.

What is needed is a device that assists a patient that has undergone a knee procedure in the post-operative rehabilitation phase which addresses the above stated shortcomings found in the art. Such a device must assist the patient in being able to gain extension and hyperextension flexibility from the knee. Additionally, such a device must be able to assist the patient in regaining leg muscle mass that may have been lost to atrophy post-surgery (and possibly pre-surgery). Such a device must minimize the risk of injury to the patient during device usage. Such a device must perform its tasks in a readily quantifiable manner so that the patient's therapists can monitor and adjust rehabilitation progress as needed.

SUMMARY OF THE INVENTION

The brace with resistance band of the present invention addresses the aforementioned needs in the art by providing a knee brace that assists a user in regaining extension and hyperextension flexibility in the knee, post-surgery or post injury, without undue pain or undue discomfort that is experienced using current rehabilitation techniques. The brace with resistance band assists the patient in regaining leg muscle mass lost due to the knee injury while reducing the potential for either anterior or posterior knee shear or other injury being occasioned upon the rehabilitating knee. Progression through the use of the brace with resistance band is quantifiable so as to allow a therapist to control the rehabilitation process and monitor the progress through rehabilitation. The brace with resistance band operates during otherwise normal wearing of a protective knee brace by the user so as to help reduce the need to attend physical therapy sessions, thereby reducing the associated time and monetary costs. The brace with resistance band is of relatively simple design and construction, being produced using standard manufacturing techniques, so as to make the device readily affordable to potential consumers for this type of system.

The resistance band used with the knee brace is readily attachable to and detachable from the knee brace so that the resistance band can be easily donned when needed and doffed when not desired, allowing the knee brace to be used in conventional fashion as well as allowing for rapid change of resistance of the system.

The brace with resistance band of the present invention is comprised of a brace that has an upper sleeve system of appropriate design that encircles an upper portion of a user limb and a lower sleeve system of appropriate design that encircles a lower portion of the user's limb, the sleeve systems being typical limb encircling members that may have a strap system to adjust the fitting and possibly the comfort level of the knee brace about the limb. A hinge system of appropriate design is attached to the upper sleeve system and to the lower sleeve system and allows pivotal articulation between the upper sleeve system and the lower sleeve system as is known in the art of braces. A first receiver is attached to the brace proximate (or directly to) the upper sleeve system on a first lateral side and anterior side of the brace while a second receiver is attached to the brace proximate (or directly to) the lower sleeve system on the first lateral side and anterior side of the brace. A third receiver may be attached to the brace proximate the upper sleeve system on a first lateral side and posterior side of the brace while a fourth receiver may be attached to the brace proximate the lower sleeve system on the first lateral side and posterior side of the brace. A resilient band has an upper end and an opposing lower end such that the upper end is attached to either the first receiver or the third receiver and the lower end is correspondingly attached to either the second receiver or the fourth receiver. The resilient band may be made from rubber or other appropriate elastomeric material. At least one pivot point may be attached to the brace between the upper receiver and the second receiver such that the resistance band passes over the pivot point. The pivot point may be a rotating pulley.

BRIEF DESCRIPTION OF THE DRAWINGS

Similar reference numerals refer to similar parts throughout the several views of the drawings.

DESCRIPTION OF THE PREFERRED EMBODIMENT

Figure 1:
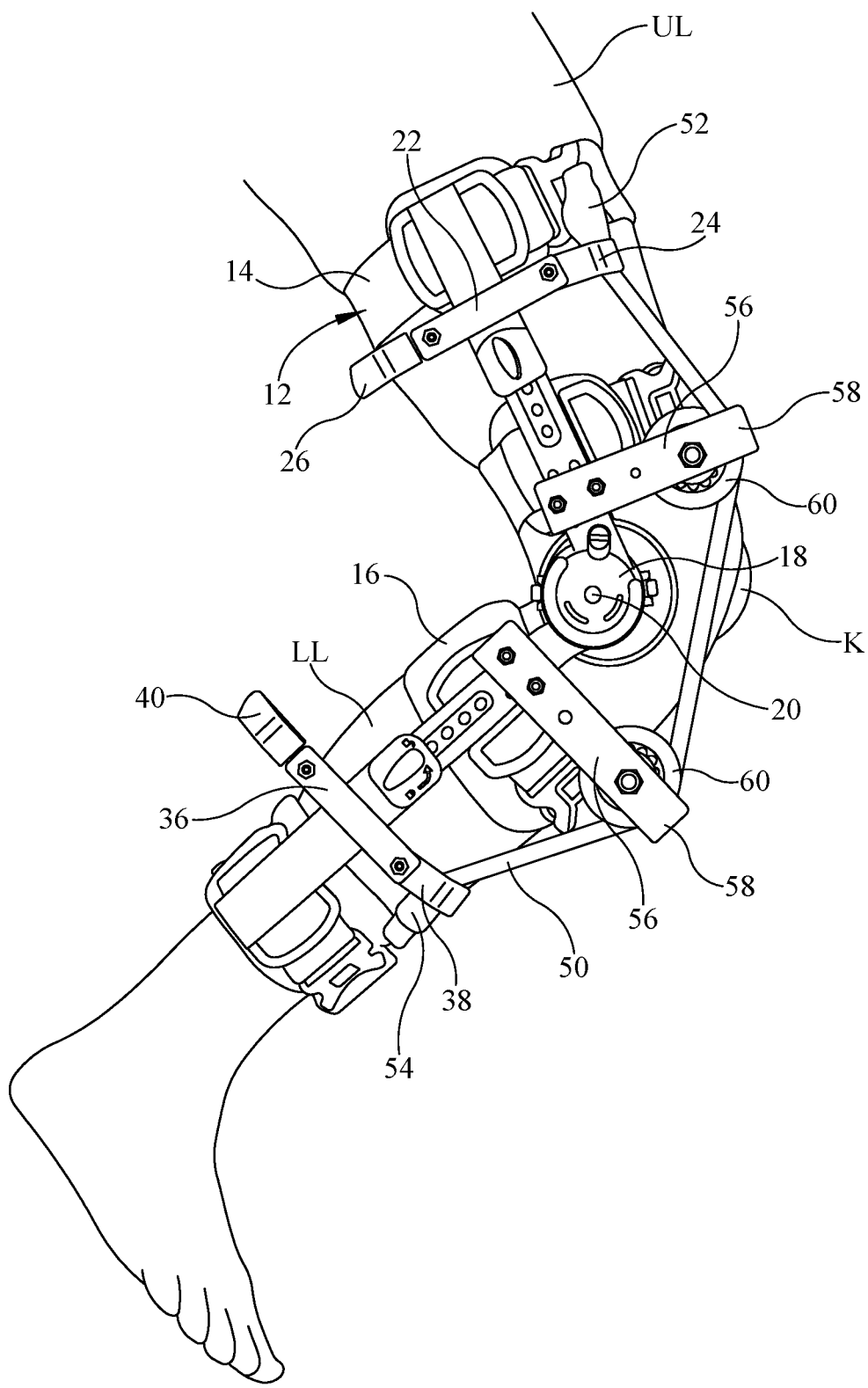
FIG. 1 is an environmental view of the brace with resistance band of the present invention with the resistance band being forward located and a user's knee being bent.

Referring now to the drawings, it is seen that the brace with resistance band of the present invention, generally denoted by reference numeral 10, is comprised of a knee brace 12 of any convention type. As seen, the typical knee brace 12 has an upper sleeve system 14 that encircles a user's upper leg UL and is secured thereat and a lower sleeve system 16 that encircles the user's lower leg LL. Appropriate sizing means may be located on each sleeve system 14 and 16 in order to assure a snug fit of the respective sleeve system about the respective portion of the user's leg. A hinge system 18 connects the upper sleeve system 14 and the lower sleeve system 16 and has a hinge point 20 that allows the upper sleeve system 14 to pivot with respect to the lower sleeve system 16 whenever the user walks or otherwise bends his or her knee K. As seen, the hinge system 18 is attached to a lateral side of the knee brace 12 such as the same or similar components are located on the opposing lateral side of the knee brace 12. Of course, the specific details of both of the sleeve systems and the hinge system can vary between knee braces depending on the manufacturer of the particular knee brace and the specific accomplishments desired by the designers of the knee brace.

One (or possibly two) upper plates 22 are attached to the knee brace 12 to the upper sleeve system 14 (or possibly to the hinge system 18) in appropriate fashion. The upper plate 22 has a first forward receiver 24 attached to a first end thereof and a first rearward receiver 26 attached to an opposing second end thereof. As seen, the first forward receiver 24 has a first vertical open passage 28 therethrough such that the cross section of a first opening 30 to this first passage 28 is smaller than the cross section of the first passage 28 itself. Similarly, the first rearward receiver 26 has a second vertical open passage 32 therethrough such that the cross section of a second opening 34 to this second passage 32 is smaller than the cross section of the second passage 32 itself.

One (or possibly two) lower plates 36 are attached to the knee brace 12 to the lower sleeve system 16 (or possibly to the hinge system 18) in appropriate fashion. The lower plate 36 has a second forward receiver 38 attached to a first end thereof and a second rearward receiver 40 attached to an opposing second end thereof. As seen, the second forward receiver 38 has a third vertical open passage 42 therethrough such that the cross section of a third opening 44 to this third passage 42 is smaller than the cross section of the third passage 42 itself. Similarly, the second rearward receiver 40 has a fourth vertical open passage 46 therethrough such that the cross section of a fourth opening 48 to this fourth passage 46 is smaller than the cross section of the fourth passage 46 itself.

The upper plate 22 and the lower plate 36 in a single plate configuration (one upper plate 22 and one lower plate 36) are each attached to the knee brace 12 in any appropriate fashion. While each plate 22 and 36 can be adhered or welded (depending on materials use to produce the appropriate components) to the knee brace 12 as appropriate, advantageously, each plate 22 and 36 is removably attached to the knee brace in order to allow usage of the present invention as desired, yet allows removal of the device when normal knee brace usage is desired. Such removable attachment of the upper plate 22 and the lower plate 36 to knee brace 12 can be accomplished in any appropriate manner known in the art such as via the usage of cooperating hook and loop material, the use of a quick disconnect clip or buckle, friction fit attachment within an appropriate receiver, a dovetail type of arrangements, etc., (none the methods illustrated), or as seen, by the introduction of a second plate (a second upper plate 22 and a second lower plate 36) and having each of the plate pairs 22 and 36 sandwich their respective portion of the knee brace 12 therebetween.

A resistance band 50 has a first bulbous end 52 and a second bulbous end 54 and is made from an appropriate resilient material such as rubber.

In order to use the brace with resistance band 10 of the present invention, the upper plate 22 and the lower plate 36 are each attached to their respective locations on the knee brace 12. A resistance band 50 having the desired level of resistance is selected and attached to the brace with resistance band 10 by passing a section of the resistance band 50 just below the first bulbous end 52 through either the first opening 30 into the first passage 28 or through the second opening 34 into the second passage 32 depending on whether the resistance band 50 is to be located on the anterior side or posterior side of the knee brace 12, which itself depends on what part of rehab is being undertaken at that point. Advantageously, the cross section of the opening 30 or 34 through which the resistance band 50 passes is slightly smaller than the cross section of the resistance band 50 at the area of insertion whenever the resistance band 50 is in a normally relaxed state so that a reasonable amount of force must be used to press the resistance band through the opening 30 or 34 which then makes removal of the resistance band 50 from the respective passage 28 or 32 also require a reasonable amount of force. The resistance band is able to be compressed (or stretched) due to its resilient nature, in order to lower its cross section so as to allow the resistance band 50 to be able pass through the appropriate opening 30 or 34. Thereafter, the opposing end of the resistance band 50 is attached to the corresponding receiver 38 or 40 in similar fashion so that a section of the resistance band 50 just about the second bulbous end 54 through either the third opening 44 into the third passage 42 or through the fourth opening 48 into the fourth passage 46 depending on whether the resistance band 50 was received within the first passage 28 or the second passage 32. Similarly, the cross section of the opening 44 or 48 through which the resistance band 50 passes is slightly smaller than the cross section of the resistance band 50 at the area of insertion so that a reasonable amount of force must be used to press the resistance band 50 through the opening 44 or 48 which then makes removal of the resistance band 50 from the respective passage 42 or 46 also require a reasonable amount of force, again, the resistance band being able to be compressed (or stretched) in order to allow the resistance band 50 to be able to pass through the appropriate opening 44 or 48 due to its resilient nature.

A second resistance band subsystem can be located on the opposing lateral side of the knee brace 12 (not illustrated).

It is noted that the resistance band can be attached to the upper plate and the lower plate in a manner other than that described above such as via a clip (not illustrated) located on the end(s) of each plate or on the ends of the resistance band. The user can use the knee brace 12 in appropriate fashion such as via walking or running or simply flexing the knee K. The resistance is provided to the knee brace 12 via the resistance band 50. This resistance aids the knee K with either extension or hyperextension flexing as the patient is walking, during flexion of the knee K by loading the hamstring, and also during extension of the knee K by loading the quadriceps. The resistance band 50 creates static tension helping hyperextend the knee K while the knee brace 12 is on the leg and unlocked to about −10 degrees, which allows the patient to prop the leg up in a similar fashion as conventional rehab, but with more incremental resistance options. If additional resistance is needed during rehab progression, then either a second resistance band 50 can be added to the device as described above, or the initial resistance band 50 is detached and a new more resistant (or less resistant) resistance band 50 is attached, such resistance band 50 swap out being relatively quick and easy.

Of course, both the upper plate 22 and the lower plate 36 may each have a single receiver or other resistance band attachment system so that the two plates are attached to the knee brace 12 with the single receiver of each plate being on either anterior or posterior side of the knee brace 12 and when it is desired to move the resistance band 50 to the opposing side of the knee brace 12, each plate is detached from the knee brace 12, rotated 180 degrees and thereafter reattached in normal fashion.

Figure 2:
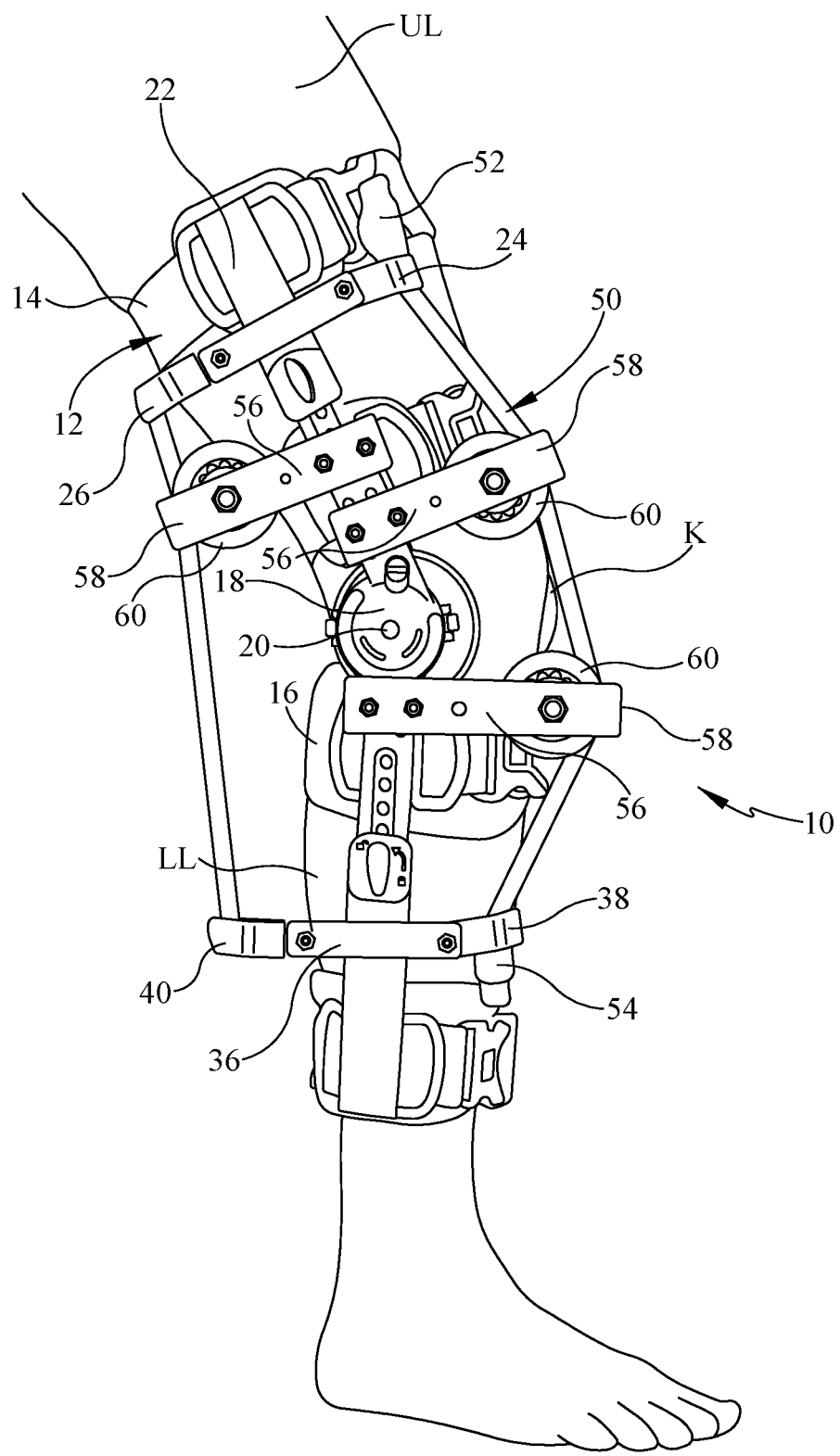
FIG. 2 is an environmental view of the brace with resistance band with the resistance band being forward located and a user's knee being relatively straightened.
Figure 3:
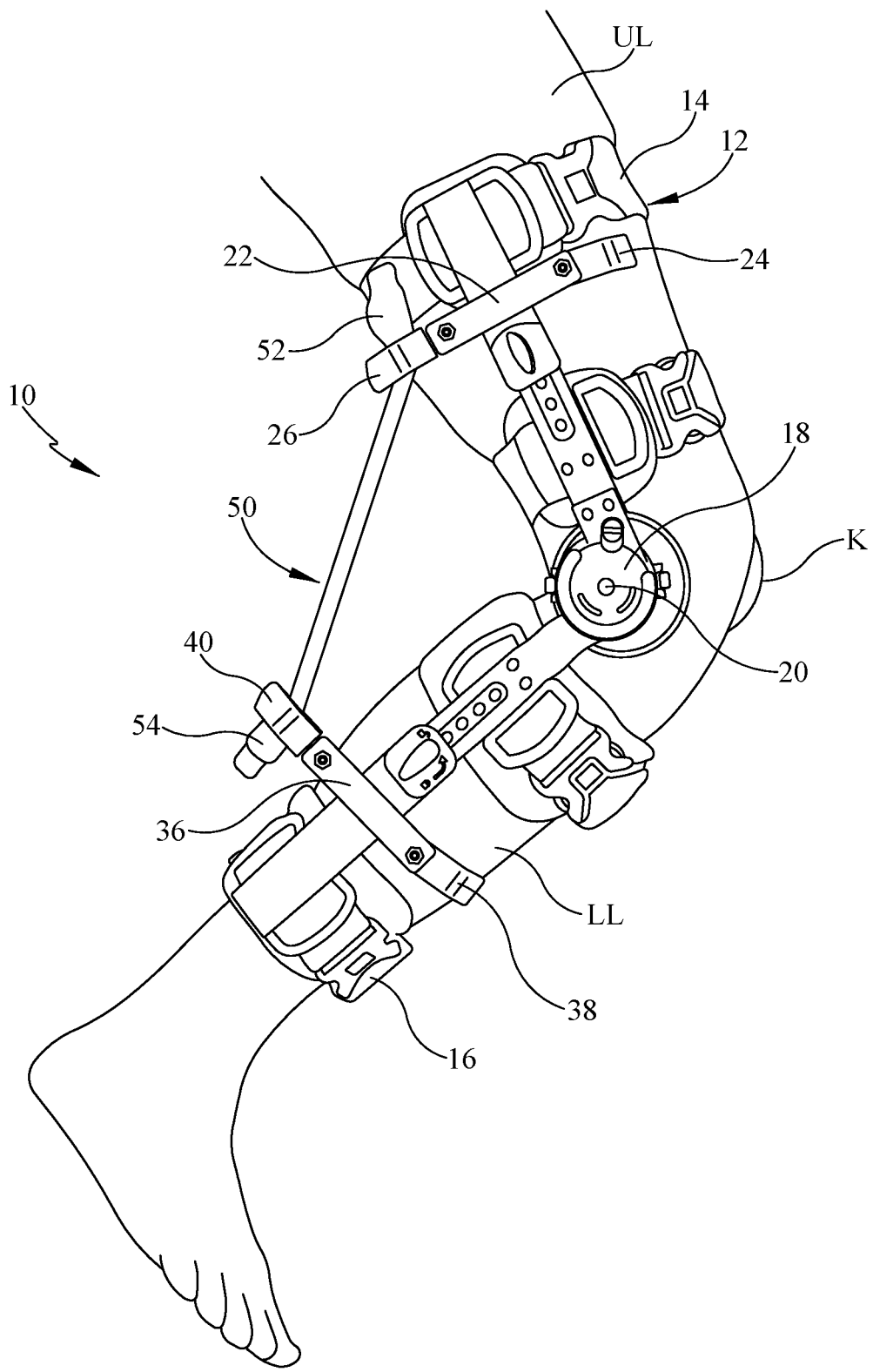
FIG. 3 is an environmental view of the brace with resistance band with the resistance band being rearward located and a user's knee being bent.
Figure 4:
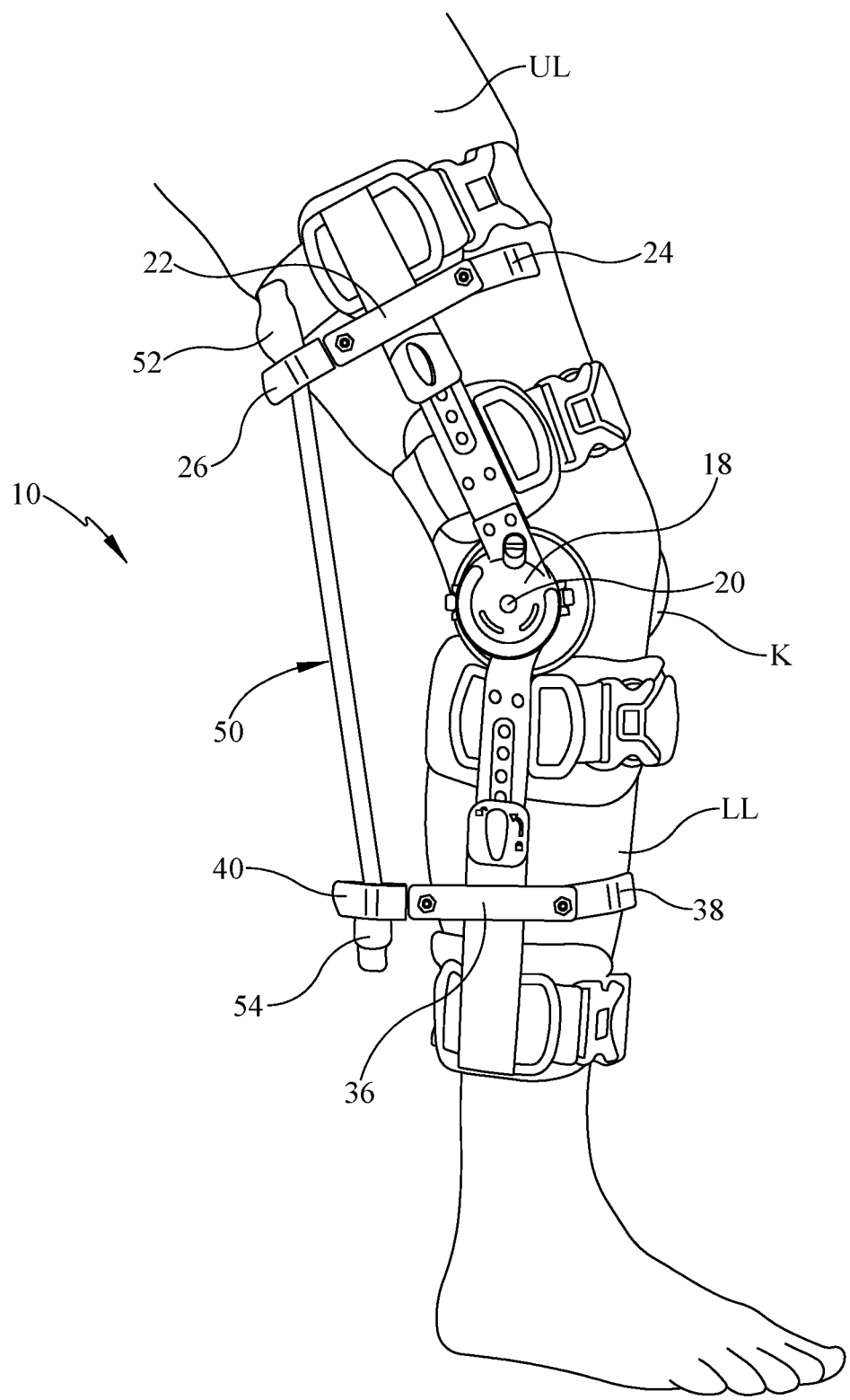
FIG. 4 is an environmental view of the brace with resistance band with the resistance band being rearward located and a user's knee being relatively straightened.
Figure 5:
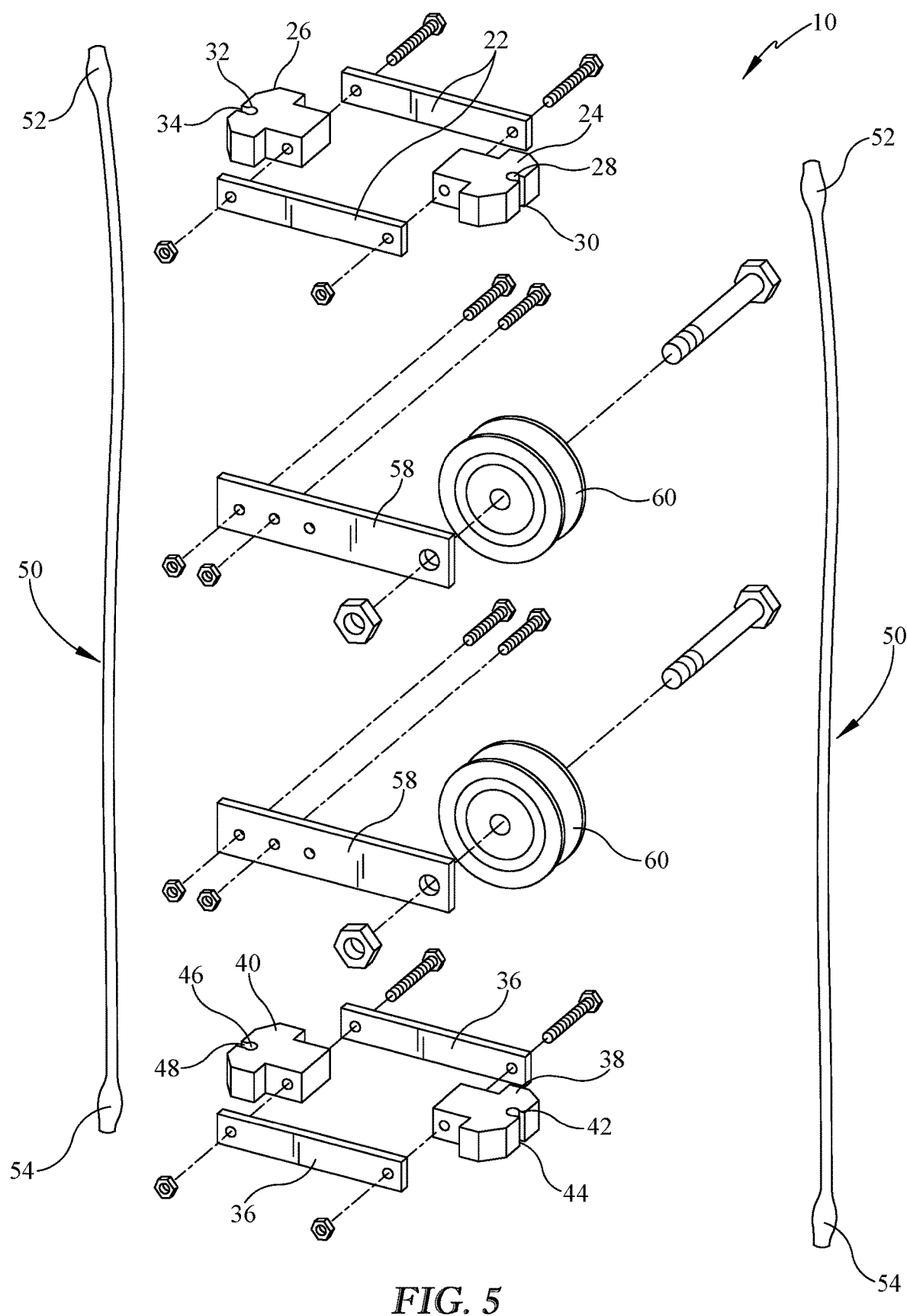
FIG. 5 is an exploded view of the brace with resistance band.

As seen in FIGS. 1, 2 and 5, one or more pivot systems 56 can be used with the brace with resistance band 10 whenever the resistance band 50 is located on the anterior side of the knee brace 12. The pivot system 56 is comprised of pivot plate(s) 58 that is attached to the knee brace 12 (either to one of the sleeve systems 14 or 16 or to the hinge system 18) in appropriate fashion. Located at an end of the pivot plate 58 is a pivot point 60 such that the resistance band 50 passes over the pivot point so that the resistance band 50 offers variable resistance when the knee K is being bent. The pivot point may be a simple rounded area over which the resistance band 50 passes or may be, as illustrated, a pulley 60 that rotates with respect to the pivot plate 58. The use of the pulley 60 instead of a fixed pivot point allows for smoother passage of the resistance band 50 over the pivot point 60 allowing for more comfortable use of the present invention. The use of the pivot systems 56 stretches the resistance band 50 an additional amount whenever the knee K is bent, thereby increasing the overall resistance provided by the resistance band 50 so as to increase the resistance loading on the knee K, expediting the rehabilitation process. Similar to the upper plate 22 and the lower plate 36, the pivot plate 58 is quickly attachable to and detachable from the knee brace 12 for easy use and discontinuance of use of this optional subsystem.

Each of the components of the brace with resistance band 10 of the present invention, with the exception of the resistance band 50, is made from an appropriate strong and sturdy material such as metal, plastic, etc.

It should be evident; the current system can be dimensionally adjusted for use about a person's upper limbs and function as an elbow brace in substantially similar fashion.

While the invention has been particularly shown and described with reference to an embodiment thereof, it will be appreciated by those skilled in the art that various changes in form and detail may be made without departing from the spirit and scope of the invention.

I claim:

1. A rehabilitation system comprising:
   a brace having an upper sleeve system adapted to encircle an upper portion of a user limb and a lower sleeve system adapted to encircle a lower portion of the user's limb such that a hinge system is attached to the upper sleeve system and to the lower sleeve system and allows pivotal articulation between the upper sleeve system and the lower sleeve system;
   a first receiver attached to the brace proximate the upper sleeve system on a first lateral side and anterior side of the brace;
   a second receiver attached to the brace proximate the lower sleeve system on the first lateral side and anterior side of the brace;
   a third receiver attached to the brace proximate the upper sleeve system on a first lateral side and posterior side of the brace;
   a fourth receiver attached to the brace proximate the lower sleeve system on the first lateral side and posterior side of the brace;

a resilient band having an upper end and an opposing lower end such that the upper end is attached to either the first receiver or third receiver and the lower end is corresponding attached to either the second receiver or the fourth receiver; and a pulley attached to the lateral side on the posterior side of the brace between the first receiver and the second receiver, such that the resistance band passes over the pulley and circumferentially slides back and forth about an outer circumference of the pulley.

2. The rehabilitation system as in claim 1 wherein the resilient band is made from rubber.

3. The rehabilitation system as in claim 1 wherein the pivot point is a rotating pulley.

\* \* \* \* \*